United States Patent [19]

Sarantakis

[11] 4,216,128

[45] Aug. 5, 1980

[54] ENKEPHALIN ANALOGUES

[75] Inventor: Dimitrios Sarantakis, West Chester, Pa.

[73] Assignee: American Home Products Corporation, New York, N.Y.

[21] Appl. No.: 54,550

[22] Filed: Jul. 5, 1979

[51] Int. Cl.$^2$ ............................................... C08L 37/00
[52] U.S. Cl. ..................................... 260/8; 424/177; 260/112.5 R
[58] Field of Search ............................ 260/112.5 R, 8; 424/177

[56] References Cited

U.S. PATENT DOCUMENTS

| | | | |
|---|---|---|---|
| 4,075,190 | 2/1978 | Sarantakis | 260/112.5 R |
| 4,103,005 | 7/1978 | Li | 260/112.5 R |
| 4,143,032 | 3/1979 | Sarantakis | 260/112.5 R |
| 4,148,785 | 4/1979 | Dheer et al. | 260/112.5 R |
| 4,148,786 | 4/1979 | Sarantakis | 260/112.5 R |
| 4,162,307 | 7/1979 | Wilkinson | 260/112.5 R |

OTHER PUBLICATIONS

Frederickson et al., Opiates and Endogenous Opioid Peptides, (1976), 239–246.
Walker et al., Science, 196 (1977) 85–87.
Bayusz et al., Febs. Letters, 76, No. 1, (1977). 91–92.

*Primary Examiner*—Delbert R. Phillips
*Attorney, Agent, or Firm*—Richard K. Jackson

[57] ABSTRACT

The polypeptides of the formula:

$$\begin{array}{c} R^1 \\ \diagdown \\ \diagup \\ R^2 \end{array} N-Tyr-D-\underset{\underset{R^4}{|}}{Cys}-Gly-N-Phe-X-R^5$$

in which
  $R^1$ is hydrogen, methyl, allyl, cyclopropylmethyl, cyclobutylmethyl or Arg;
  $R^2$ is hydrogen or methyl;
  $R^3$ is hydrogen, (lower) alkylthio or a repeating unit of the depicted polypeptide forming a dimeric dithio ether;
  $R^4$ is hydrogen or methyl;
  X is D-Ser, D-Thr, D-Asn, D-Asp, D-Gln, D-Glu, D-His, D-Lys, D-Arg, D-Leu and D-Met;
  and $R^5$ represents hydroxyl, (lower) alkyl ester amide or (lower)alkyl amide of the 1-carboxyl group of the C-terminal amino acid or a —CH$_2$OH group replacing said 1-carboxyl group, or a pharmaceutically acceptable salt thereof, exert an analgesic effect in warm-blooded animals.

6 Claims, No Drawings

ENKEPHALIN ANALOGUES

BACKGROUND OF THE INVENTION

Enkephalin, a natural opiate receptor agonist in the brain, has been identified [see Hughes et al., *Nature*, 256 577 (1976)] as a mixture of two pentapeptides: H-Tyr-Gly-Gly-Phe-Met-OH (methionine-enkephalin) and H-Tyr-Gly-Gly-Phe-Leu-OH (leucine-enkephalin). Both peptides mimic the ability of morphine to block electrically evoked contractions of mouse vas deferens and guinea pig ileum, and both inhibit the sterospecific receptor binding of the opiate antagonist 3H-naloxone in brain homogenates.

It has been proposed that enkephalin receptors may be sites at which morphine-like drugs exert their analgesic activities, and that enkephalin may be the modulator or transmittor in brain systems for pain suppression or analgesia. It has been reported that methionine-enkephalin and leucine-enkephalin, when administered by injection in the brain ventricle in rats, induce a profound analgesia that is fully reversible by naloxone. [See Beluzzi et al., *Nature*, 260, 625 (1976)]. The naturally occurring enkephalins are inactive when administered peripherally, presumably because they are rapidly destroyed by blood enzymes and/or are poorly transported across the blood-brain barrier.

The amino acid sequence of methionine-enkephalin is identical to that of the N-terminal portion of the C-fragment (β-endorphin or α-LPH[61–91]) of the peptide β-lipotropin, which is found in large concentrations in the pituitary and in much lower concentrations in the brain. Other naturally-occurring fragments of β-lipotropin are known, for example: α-endorphin (β-LPH[61–76]) and γ-endorphin (β-LPH[61–77]). Both βlipotropin and the endorphins show morphine-like properties in various test systems, and it has been suggested that methionine-enkephalin is a breakdown product of the large opiate-like peptides. Enkephalin, its relationship to β-lipotropin and the endorphins, and the pharmacological properties thereof, are reviewed in an article by Iversen et al., *Nature*, 262, 738 (1976). Recent developments are also described in detail in the "Proceedings of the International Narcotics Research Club Meeting, Abderdeen, U.K., July 19–22, 1976," published in *OPIATES AND ENDOGENOUS OPIOID PEPTIDES*, North Holland Publishing Company, Amsterdam, 1976.

Various structural variations of methionine-enkephalin and leucine-enkephalin are described in the literature. For example, the pentapeptide H-Tyr-Gly-Gly-Phe-Thr-OH, wherein the fifth amino acid residue (methionine or leucine) is replaced by threonine, is described by Chang et al., Life Sciences, 18, 1473(1976). Similarly, a long acting synthetic pentapeptide, Tyr-D-Ala-Gly-Phe-Met-amide is described in Pert et al., Science, 194, 330 (1976); which compound, like the natural enkephalins, is reportedly inactive when administered peripherally. Baxter et al., British Journal of Pharmacology, March 2, 1977, pages 455P–456P and 523P report activity in the compound Tyr-D-Ala-Gly-Phe-D-Leu when administered intracerebroventricularly. Coy et al. B.B.R.C. 73 632 (1976) disclose that D-Met[5] enkephalin has one tenth the activity of Met enkephalin. Bajusz et al. FEBS Letters 76, 91 (1977) by replacing Gly[2] with D-Met and the Met[5] by Pro-NH2 obtained a very potent antinociceptive pentapeptide Tyr-D-Met-Gly-Phe-Pro-NH2 which was 5.5 times more potent than morphine by intravenous administration.

Romer et al., Nature, 268 547 (1977) showed that the substituted tetrapeptide amide

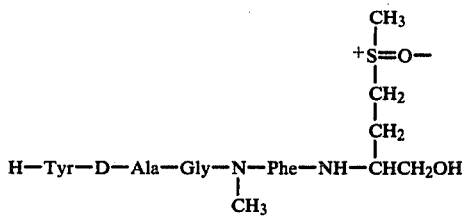

possesses potent peripheral analgesic activity and some analgesic activity when given orally at high doses (200–300 mg/kg).

Morgan et al., "Peptides", Proc. Fifth Amer. Pept. Symp. ed. Goodman and Meienhofer, p. 111 (1977) reported in vitro and in vivo biological activities of several enkephalin analogs among which was N(Me)-Tyr-Gly-Gly-Phe-Met-NH-Propyl. Ling et al., ibid., p. 96 (1977) reported in vitro activities of several analogs of enkephalin with D-amino acids in position 5.

Dutta et al., Life Sciences 21, 559 (1977) and Dutta et al., Acta. Pharm. Science 14, 14 (1977) described several analogs with D-Ser, D-Met, D-Ala, D-Thr, D-Lys(Boc), D-Phe, D-Leu, D-Asp and D-Ser(t-Bu), at position 2 and various substitutions with L-amino acids or amines at position 5.

U.S. Pat. No. 4,148,786 discloses:

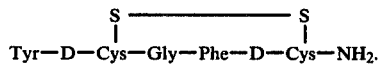

Belluzzi et al., Life Sciences, 23, 99 (1978) described analogs with D-Ala at position 2 and D-Leu or D-Met at position 5.

DESCRIPTION OF THE INVENTION

In accordance with this invention, there is provided a group of polypeptides of the formula:

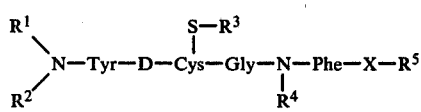

in which $R^1$ is hydrogen, methyl, allyl, cyclopropylmethyl, cyclobutylmethyl or Arg;

$R^2$ is hydrogen or methyl;

$R^3$ is hydrogen, (lower)alkylthio or a repeating unit of the depicted polypeptide forming a dimeric dithio ether;

$R^4$ is hydrogen or methyl;

X is D-Ser, D-Thr, D-Asn, D-Asp, D-Gln, D-Glu, D-His, D-Lys, D-Arg, D-Leu or D-Met;

and $R^5$ represents hydroxyl, (lower)alkyl ester, amide or (lower)alkyl amide of the 1-carboxyl group of the C-terminal amino acid or a —CH2OH group replacing said 1-carboxyl group, or a pharmaceutically acceptable salt thereof.

The pharmaceutically acceptable salts of the polypeptides of this invention are acid addition salts of the free base in which the acid may be either organic or inorganic, as for example, hydrochloric, phosphoric, maleic, acetic, citric, succinic, malic, and similar acids. Likewise, salts of the free peptidic acid are embraced by the expression "pharmaceutically acceptable salts", and include the sodium, potassium, ammonium, and lower alkylamine salts. The salts are prepared and isolated by conventional methods. In addition, the expression (lower)alkyl, used throughout this specification and in the appended claims, is intended to embrace alkyl groups containing from 1 to about 6 carbon atoms.

The analgesic polypeptides of this invention are prepared by classical and/or typical solid phase procedures employing either a benzhydrylamine polystyrene based resin for the production of the C-terminal amides or a chloromethylated or hydroxy methylated divinyl benzene crosslinked polystyrene resin for production of the C-terminal carboxylic acids, esters or lower alkylamides. The polypeptide is removed from the resin support with HF and purified by gel filtration. Conversion of the 1-carboxy group of the C-terminal amino acid to the —CH$_2$OH group is performed conventionally.

The N-substituted tyrosine and phenylalanine reactants employed in the production of the compounds disclosed herein are readily prepared by reaction of methylchloride, allylchloride, cyclopropylmethylchloride or cyclobutylmethylchloride with a Boc-tyrosyl ester or Boc-phenylalanine ester in the presence of silver oxide. The product is then saponified and hydrolyzed to obtain the desired reactant.

The analgesic activity of the polypeptides of this invention was demonstrated following a modification of the phenylbenzoquinone induced writhing test procedure of Siegmund et al., Proc. Soc. exp. Biol. Med. 95, 729–731 (1957), in which groups of ten CF-1 mice were administered, subcutaneously, known dosages of N(Me)Tyr-D-Cys-Gly-N(Me)Phe-D-Ser-NH$_2$, as a compound representative of the group of compounds of this invention, ranging from 0.178 mg/kg to 3.2 mg/kg. Five minutes later, each animal received, i.p., 0.25 ml. of a 0.02 percent phenylbenzoquinone solution. The animals were observed over a ten minute period following the phenylbenzoquinone injection for the presence of writhing. Animals not writhing were considered to exhibit analgesia. The dose-response analysis was then performed according to Litchfield et al., J. Pharmacol. exp. Therap. 96, 99–113 (1949). The ED$_{50}$ for the test compound was 0.85 mg/kg (0.47–1.53) at 15 minutes by subcutaneous administration. Following the same procedure, analgesia was observed at a dose of 10 mg/kg for a period of forty five minutes in 100 percent of the animals. At a dose of 0.56 mg/kg 50 percent demonstrated analgesia at 15 minutes; 40 percent at 30 minutes and 30 percent at 45 minutes. Similarly, 50 percent of a group of 10 mice demonstrated analgesia for 30 minutes at an oral dose of 50 mg/kg. The same compound, demonstrated a relative displacement potency twenty six times that of morphine following the procedure of Chang et al., Life Sciences 18, 1473–82 (1976).

Similarly, the product of Example 4 exhibited a relative displacement potency two times that of morphine in the procedure of Chang et al., loc. cit., an ED$_{50}$ of 0.64 (0.29–1.4) mg/kg at 15 minutes, subcutaneous injection and 10 percent analgesia at a dose of 50 mg/kg in 30 minutes after oral administration.

The test results demonstrate that the compounds of this invention induce analgesia upon administration of a single subcutaneous injection of about 0.6 milligrams per kilogram or more. For practical purposes, it is contemplated, based upon the preceding test results, that a unit dose of from about 0.5 to about 20 milligrams per kilogram for single or plural administration(s) is the appropriate dosage to achieve that degree of analgesia desired for various application. By oral administration, a dosage of up to about 400 milligram per kilogram or more, produce the desired effect. The exact dose to be employed will, of course, vary somewhat with the specific compound employed, the patient and the degree of analgesia desired. The determination of a precise dose for production of a desired effect is readily determined empirically by the physician. The route of administration, whether subcutaneous, intravenous, intramuscular or oral, etc., also must be considered by the physician using the compounds disclosed herein because the degree of response obviously related to the route of administration.

The protected intermediate peptidoresin intermediates for the disclosed polypeptides form an additional aspect of the invention. The intermediates are of the formula:

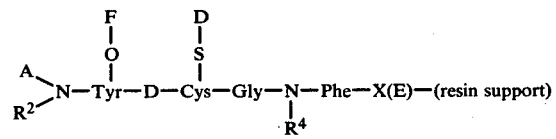

in which

R$^2$, R$^4$ and X are defined supra;

A is hydrogen or an α-amino protecting group or alpha amino protected N-guanyl protected arginyl;

F is a protecting group for the phenolic hydroxy group of tyrosyl;

D is a protecting group for the mercapto group of D-cysteinyl, and E is a protecting group for side chain reactive substituents of the C-terminal amino acid moiety.

Of the many protecting groups known to the art for use in conjunction with each of the functional groups found in the depicted polypeptide intermediate, the most preferred are tert-butyloxycarbonyl (Boc) for the α-amino group of the arginyl or tyrosyl moiety, nitro (NO$_2$) for the guanyl group of the arginyl moiety, 2,6-dichlorobenzyl (Cl$_2$Bzl) for the phenolic hydroxyl group of the tyrosyl moiety, p-methoxybenzyl (MBzl) for the mercapto group of the D-cysteinyl moiety, and for the C-terminal amino acids, benzyl for the hydroxy group of D-Seryl and D-threonyl, tosyl for the N$^{im}$ atom of D-histidyl, 2-chlorobenzyloxycarbonyl for the amino group of D-lysyl and nitro for the N$^g$ atom of arginyl. Because the C-terminal amides are the preferred final products, the resin support in the intermediates is preferably a benzhydrylamine polystyrene resin.

The following examples detail the preparation of representative compounds of this invention by way of illustration:

EXAMPLE 1

N$^\alpha$-tert-Butyloxycarbonyl-N$^\alpha$-methyl-O-2,6-dichlorobenzyl-L-tyrosyl-S-p-methoxybenzyl-D-cysteinyl-glycyl-N-methyl-L-phenylalanyl-O-benzyl-D-seryl-benzhydrylamine polystyrene resin Benzhydrylamine polystyrene resin hydrochloride (Bachem. Inc.) (8 g.) of approximate content of free amino groups 0.4 mmoles/g. was placed in a reaction vessel of a peptide synthesizer Beckman 990A, and subjected to subsequent cycles of amino group deprotections and amino acid couplings as described in Program 1 and Program 2. The last program was performed in order to insure complete coupling of each amino acid. The following amino acids were incorporated onto the benzhydrylamine resin as described above: Boc-D-Ser(Bzl)-OH, Boc-N-Me-Phe-OH, Boc-Gly-OH, Boc-D-Cys(SMBzl)-OH and Boc-N-Me-Tyr(Cl$_2$Bzl)OH, to afford the title peptidoresin.

Program No. 1

Peptide Synthesizer, Beckman 990

1. Wash with CH$_2$Cl$_2\times$3.
2. Treat with TFA-CH$_2$Cl$_2$-EDT, 1:1:5% for 5 min.
3. Repeat (2) for 25 min.
4. Wash with CH$_2$Cl$_2\times$4.
5. Treat with TEA 12% in DMF for 1 min.
6. Repeat (5) for 5 min.
7. Wash with CH$_2$Cl$_2\times$3.
8. Add 4 equivalents of Boc-protected amino acid and stir for 5 min.
9. Add 2 equivalents of 1M-DIC solution in DMF and stir for 25 min.
10. Add 2 equivalents of 1M-DIC solution in DMF and stir for 180 min.
11. Wash with CH$_2$Cl$_2\times$3.
12. Wash with methanol$\times$3.
13. Wash with CH$_2$Cl$_2\times$3.

Program No. 2

Peptide Synthesizer, Beckman 990

1. Wash with CH$_2$Cl$_2\times$3.
2. Add 2 equivalents of Boc-protected amino acid and stir for 5 min.
3. Add 2 equivalents of 1M-DIC solution in DMF and stir for 180 min.
4. Wash with DMF$\times$3.
5. Wash with CH$_2$Cl$_2\times$3.
6. Wash with methanol$\times$3.
7. Wash with CH$_2$Cl$_2\times$3.

EXAMPLE 2

N-Methyl-L-tyrosyl-D-cysteinyl-glycyl-N-methyl-L-phenylalanyl-D-seryl amide

The peptidoresin of the previous example (11 g.) was mixed with anisole (20 ml.) and treated with liquid HF (200 ml.) in an ice-bath and under vacuo for 55 minutes. The excess HF was evaporated under reduced pressure as fast as possible, ca. 60 minutes, and the residue was taken in 10% aqueous acetic acid (200 ml.) filtered and the filtrate lyophilized to a fluffy solid. The crude material was chromatographed through a column (2.5$\times$90 cm) of Sephadex G-10 and eluted with 5% aqueous acetic acid. Fractions of 4.5 ml. were collected and the fractions in tubes 61-70 were pooled and lyophilized to yield 760 mg. of the title compound.

TLC silica gel precoated glass plates Merck.
$R_f$(BuOH-Water-AcOH, 4:1:1, v/v) 0.45.
$R_f$(BuOH-EtOAc-Water-AcOH, 1:1:1:1, v/v) 0.75.

Amino acid analysis: Ser(1) 1.16, Gly (1) 1, Cys (1) 0.39. N-Me-Tyr and N-Me-Phe ND.

EXAMPLE 3

N-tert-Butyloxycarbonyl-N-methyl-O-2,6-dichlorobenzyl-L-tyrosyl-S-p-methoxybenzyl-D-cysteinyl-glycyl-N-methyl-L-phenylalanyl-D-asparaginyl benzhydrylamine polystyrene resin The title peptidoresin was prepared in a similar fashion to Example 1 with the exception that Boc-D-asparagine was initially reacted with the benzhydrylamine polystyrene resin.

EXAMPLE 4

N-Methyl-L-tyrosyl-D-cysteinyl-glycyl-N-methyl-L-phenylalanyl-D-asparagine amide The peptidoresin of the previous example (ca. 12 g.) was mixed with anisole (ca. 20 ml.) and treated with 200 ml. liquid anhydrous HF for 1 hour under exclusion of air and under cooling (ice-bath). The HF mixture was evaporated to dryness and the residue was taken in 10% aq. AcOH and filtered. The filtrate was treated with Bio Rad AG 3 (acetate form) and lyophilized to yield a gummy residue which was chromatographed through a column (2.5$\times$90 cm) of Sephadex G10. The desired compound was eluted with 5% aq. AcOH between fractions (110 drops each) 48 to 61, to afford 1.39 g. of the title pentapeptide.

TLC silica gel precoated glass plates Merck
$R_f$(n-BuOH-water-AcOH, 4:1:1, v/v) 0.26.
$R_f$(n-BuOH-EtOAc-Water-AcOH, 1:1:1:1, v/v) 0.52. (trace of impurity at $R_f$0.55).

Amino acid analysis: Asp(1) 0.98, Gly (1) 1, Cys (1) 0.27, NH$_3$(2) 2.61, N-Me-Tyr, N-Me-Phe, ND.

What is claimed is:

1. A polypeptide of the formula:

$$\begin{array}{c} R^1 \\ \phantom{R^1}\diagdown \\ \phantom{RRR}N\text{—Tyr—D—Cys—Gly—N—Phe—X—R}^5 \\ \phantom{R^1}\diagup \phantom{RRRRRRRRRRRRRRR} | \\ R^2 \phantom{RRRRRRRRRRRRRRRR} R^4 \end{array} \quad \begin{array}{c} S\text{—R}^3 \\ | \\ \\ \\ \end{array}$$

in which
R$^1$ is hydrogen, methyl, allyl, cyclopropylmethyl, cyclobutylmethyl or Arg;
R$^2$ is hydrogen or methyl;
R$^3$ is hydrogen, (lower)alkylthio or a repeating unit of the depicted polypeptide forming a dimeric dithioether;
R$^4$ is hydrogen or methyl;
X is D-ser, D-Thr, D-Asn, D-Asp, D-Gln, D-Glu, D-His, D-Lys, or D-Arg;
and R$^5$ is the hydroxyl moiety of the 1-carboxyl group of the C-terminal amino acid or a (lower)alkyl ester, amide or (lower)alkyl amide thereof or a —CH$_2$OH group replacing said 1-carboxyl group, and their protected peptidoresin intermediates, or a pharmaceutically acceptable salt thereof.

2. The compound of claim 1 which is N-methyl-L-tyrosyl-D-cysteinyl-glycyl-N-methyl-L-phenylalanyl-D-seryl amide or a pharmaceutically acceptable salt thereof.

3. The compound of claim 1 which is N-methyl-L-tyrosyl-D-cysteinyl-glycyl-N-methyl-L-phenylalanyl-D-asparagine amide.

4. A protected peptidoresin of claim 1 of the formula:

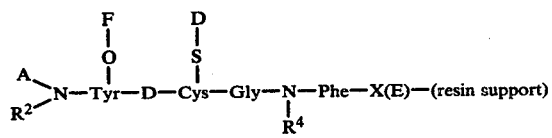

in which
- A is hydrogen or an alpha amino protecting group or alpha amino protected N-guanyl protected arginyl;
- $R^2$ is hydrogen or methyl;
- F is a protecting group for the phenolic hydroxy group of tyrosyl;
- D is a protecting group for the mercapto group of D-cysteinyl;
- $R^4$ is hydrogen or methyl;
- X is D-Ser, D-Thr, D-Asn, D-Asp, D-Gln, D-Glu, D-His, D-Lys, or D-Arg;
- and E is a protecting group for the side chain reactive substituents of the C-terminal amino acid X.

5. The compound of claim 4 which is $N^\alpha$-tert-Butyloxycarbonyl-$N^\alpha$-methyl-O-2,6-dichlorobenzyl-L-tyrosyl-S-p-methoxybenzyl-D-cysteinyl-glycyl-N-methyl-L-phenylalanyl-O-benzyl-D-seryl-benzhydrylamine polystyrene resin.

6. The compound of claim 4 which is N-tert-Butyloxycarbonyl-N-methyl-O-2,6-dichlorobenzyl-L-tyrosyl-S-p-methoxybenzyl-D-cysteinyl-glycyl-N-methyl-L-phenylalanyl-D-asparaginyl benzhydrylamine polystyrene resin.

* * * * *